(12) United States Patent
Brunner et al.

(10) Patent No.: US 6,433,868 B1
(45) Date of Patent: Aug. 13, 2002

(54) METHOD FOR DIFFERENTIAL SPECTROSCOPIC MEASUREMENTS

(75) Inventors: Herwig Brunner, Stuttgart; Jürgen Bernhagen, Tübingen; Frank Vitzthum, Hildrizhausen, all of (DE)

(73) Assignee: Fraunhofer-Gesellschaft zur Förderung der Angewandten Forschung E.V. (DE)

(*) Notice: Subject to any disclaimer, the term of this patent is extended or adjusted under 35 U.S.C. 154(b) by 14 days.

(21) Appl. No.: 09/673,459
(22) PCT Filed: Feb. 11, 2000
(86) PCT No.: PCT/EP00/01121
§ 371 (c)(1),
(2), (4) Date: Dec. 30, 2000
(87) PCT Pub. No.: WO00/49393
PCT Pub. Date: Aug. 24, 2000

(30) Foreign Application Priority Data

Feb. 15, 1999 (DE) .......................................... 199 06 264

(51) Int. Cl.⁷ ................................................ G01N 1/10
(52) U.S. Cl. ...................... 356/300; 356/246; 436/164; 436/165
(58) Field of Search .................................. 436/164, 165, 436/171, 807, 809; 422/100; 356/300–334, 246

(56) References Cited

U.S. PATENT DOCUMENTS

| 4,668,617 A | * | 5/1987 | Furuta et al. ................... 435/4 |
| 4,828,386 A | * | 5/1989 | Matkovich et al. .......... 356/246 |
| 4,948,564 A | | 8/1990 | Lyman et al. |
| 6,054,711 A | * | 4/2000 | Bruening et al. ...... 250/339.08 |

FOREIGN PATENT DOCUMENTS

| DE | 231649 A1 | 1/1986 |
| DE | 4405375 | 8/1995 |
| EP | 0545673 | 6/1993 |
| GB | 1499414 | 2/1978 |
| GB | 2218511 A | 11/1989 |

OTHER PUBLICATIONS

Geiger et al. "Standardized Measurements and Differemtial Spectroscopy in Microplates", Anal. Biochem., 2001, 296, 29–40.*

* cited by examiner

Primary Examiner—Jill Warden
Assistant Examiner—Yelena Gakh
(74) Attorney, Agent, or Firm—Ostrolenk, Faber, Gerb & Soffen, LLP

(57) ABSTRACT

The patent relates to a method for spectroscopic and spectrofluorimetric determination of the interaction between materials. The determination takes place using apparatus consisting of several basins.

6 Claims, 2 Drawing Sheets

METHOD FOR DIFFERENTIAL SPECTROSCOPIC MEASUREMENTS

BACKGROUND OF THE INVENTION

The present invention relates to a process for the differential spectroscopical and differential fluorometric determination of the interaction of substances with the aid of a microtitration plate and to the use of a microtitration plate for the differential spectroscopical and differential fluorometric determination of the interaction of substances.

The spectrophotometric determination of substances in homogeneous solutions is important in a large number of fields, e.g., in analyses of the environment, in basic research, in medical diagnostics, in forensic studies, etc. In the course of these determinations, substances such as nucleic acids, proteins, enzymes, their substrates, etc. are determined, ie., their presence is established and/or quantified. In these cases, it is often of interest to determine the interaction of various substances with each other. Differential spectrophotometry or differential fluorometry can be used to detect the interaction of substances with each other by way of their changed spectral or fluorometric properties. The spectral or fluorometric changes are caused either by direct interaction of the substances with each other or by binding induced configuration changes.

Similarly, solvent dependent configuration changes can be detected or aggregation equilibria can be observed in dependence upon the medium and the concentrations of substances.

Differential spectrophotometric or differential fluorometric measurements are usually made with the aid of two tandem cuvettes, namely a sample cell and a reference cell. A tandem cuvette comprises two chambers separated by a vertical partition. The solution of a first substance is put with identical concentrations into one chamber of each the sample cell and the reference cell for differential spectrophotometric or differential fluorometric measurements. The two other chambers are filled with buffer solution. In the subsequent measurement, which is made with a horizontal light beam passing through both chambers, identical spectrophotometric and fluorometric properties of the two tandem cuvettes must be observed. After that, a well defined amount of a second substance is added to the solution of the first substance in the sample cell and the same amount is filled into the buffer filled chamber of the reference cell in order to compensate for ligand absorption or ligand fluorescence. In order to avoid concentration differences, identical amounts of the buffer solution must be added to the solution of the first substance in the reference cell. After that, as described above, measurements are made a second time and the readings are compared. In view of the usually low spectral and fluorometric changes, this method is very sensitive in regard to concentration differences and therefore the respective additions of the second substance must be small as far as their volume is concerned. The limit of the determinations is given by the solubility of the substance in the buffer. Finally, when the substances are mixed, care must be taken that no solution is removed from the cells.

SUMMARY OF THE INVENTION

The technological problem underlying the present invention is to provide a process which overcomes the above cited shortcomings, in particular, minimises concentration effects in order to increase the sensitivity of the measurements, and which is capable of analysing substances of low solubility and of reducing errors due to mixing, as well as of facilitating rapid, universally applicable, parallel and therefore low cost determinations of interactions of substances.

The present invention solves the technological problem by providing a process for determining the differential spectroscopical and fluorometric interaction of at least two different substances by means of a microtitration plate containing a plurality of small bowls, wherein a lid with at least one trough associated with one small bowl is associated with the microtitration plate, and wherein a first solution of a first substance is placed into a small bowl, a second solution of a second substance is placed into the trough associated with the small bowl, and a third solution containing a mixture of the first substance and the second substance is placed into a further trough and/or further small bowl so that subsequently the differential spectroscopical and/or differential fluorometric determination can be carried out by vertical irradiation through the filled trough and the small bowls with electromagnetic waves. Conventional photometers and fluorometers, ie., ELISA or MTP readers can be used for these measurements. Thus, the invention provides that two different substances are arranged separated from each other in vertically superimposed relationship in a region characterised as the reference region, whereas the mixture of the substances is situated in a sample region of the microtitration plate and can be analysed at the same time.

If the first substance interacts with the second substance, accompanied by a change in the spectral and/or fluorometric properties, the extinction coefficients or the fluorescence characteristics of at least one of the substances in the third solution changes, ie., in the mixture of the two solutions, in comparison with the reading obtained from the two separate solutions. These changes in the extinction coefficient allow conclusions about the substance interactions and the substance properties and structures. The extinction coefficients or the fluorescence characteristics are constant if there is no interaction or in null balance.

With the identical geometrical features preferred in accordance with the invention for the small bowls of the microtitration plate and the troughs in the lid, there are identical absorptions in the sample region, ie., in the region of the microtitration plate in which the trough containing the mixture of the first and the second solution is situated, and the reference region, ie., in the region of the microtitration plate in which the first and the second solution are arranged separated from each other and in superimposed relationship in trough and small bowls, provided that no solutions were filled in. If the geometrical features.of the respective small bowls or troughs are nonidentical, a geometrical factor must be introduced in the determination of the absorption.

In a particularly preferred embodiment, the invention relates to the aforementioned process, wherein the third solution is provided by mixing a solution of the first substance with a solution of the second substance, with the volume and/or substance concentrations of the two solutions used for the preparation of the third solution each being equal to those of the first and of the second solution.

In a further preferred embodiment, the invention relates to an aforementioned process, wherein the height of the third solution layer in the small bowl or the trough containing the third solution is equal to the sum of the heights of the layers of the first and the second solution in the small bowl and in the trough in which these solutions are situated.

In a further preferred embodiment. the invention provides that the heights of the filled in first, second, and/or third solutions are standardised, ie., that the development of menisci or reading errors resulting from different levels of filling of the solutions are precluded by using in accordance with the invention a lid with at least one trough, wherein the base section of this trough ensures a well defined length of the light path in the small bowl from the base portion of the small bowl to the base section of the trough arranged on top.

The present invention envisages the use of a microtitration plate containing a plurality of small bowls, with at least part of the microtitration plate covered by a lid having at least one trough associated with a small bowl. The essential features of such sample carrier systems have been described, for example, in DE 44 05 375 A1 which, as far as the production and the structure of such sample carrier systems is concerned, is included in the present disclosure.

Thus, the invention makes use of a sample carrier system comprising two elements, namely a microtitration plate and a lid associated with this microtitration plate.

The lid includes at least one trough having one or more sidewalls and a base section, preferably a plurality of troughs, each formed by sidewalls and a base section and interconnected with the others via a base plate and/or frame member. The lid can cover the microtitration plate partially or completely, and it can be provided that only regions of the lid have troughs with which small bowls are associated, with other regions of the lid being planar. The lid is associated with the microtitration plate in a fashion such that it can be plugged onto the same or laid down on the same, with the troughs of the lid extending from above into the openings of the small bowls of the microtitration plate or engaging the same, ie., being associated with the same. However, the lid can also be adapted to be folded up or folded down at the microtitration plate, e.g., by means of hinges, can be integral with the microtitration plate or can be associated permanently with the same in some other way, wherein one opening for filling the small bowls must be provided in each of the latter two embodiments.

It can be provided in one embodiment that the lid has a single trough composed of a base section, sidewalls, and, optionally, a circumferential folded rim or collar, wherein the base plate of the lid covers in planar fashion the remaining part of the microtitration plate either completely or partially. This lid with a single trough can be used in combination with various microtitration plates. When microtitration plates with the conventional shape of the small bowls or appropriately shaped small bowls of novel microtitration plates. are used, the upper rim or the collar of the lid serves as a support surface on the microtitration plate. Also the bottom of the lid of the present invention can be used as a support surface on the microtitration plate with an appropriately adapted shape of the small bowls of the microtitration plate.

The base plate of the lid can be configured as a web and/or advantageously comprises a frame member fully or partially embracing the microtitration plate, with the frame member serving for plugging the lid onto a microtitration plate and keeping the lid in stationary position on the microtitration plate. The lid can bear troughs arranged in the form of a row, ie., it can be composed of troughs arranged in succession. However, it can also be provided that the lid comprises troughs in the form of a matrix. Of course, the invention also provides that such a lid covers only regions, e.g., a row on a microtitration plate, le., that it is associated with the same. Accordingly, a lid, which makes up a row, can be associated with a row of small bowls on a microtitration plate. But it can also be provided to associate a lid configured as a matrix with a microtitration plate in the form of a matrix, with the lid covering all the small bowls of the microtitration plate.

The specific form of the lid depends upon the form of the conventional or novel microtitration plate used.

It is particularly preferred to practice the process with a microtitration lid which covers some of the small bowls of the microtitration plate in planar fashion, ie., without troughs, and forms in his way a sample region of the subjacent microtitration plate, with an other part of the lid having troughs associated with individual small bowls and covering the reference region of the microtitration plate. In the sample region of the microtitration plate, where therefore no superimposed positioning of samples is allowed, the third solution, ie., the mixture of the first and the second substance, is filled in, whereas the first and the second solution can be filled in superimposed relationship and separated from each other into the small bowls of the reference region into which the troughs extend.

Of course, it is also possible to provide a lid which has troughs in the sample region of the microtitration plate. In this case, it can also be provided in accordance with the invention to fill the third solution only into the trough of the lid rather than into the small bowl proper or into both, ie., into the small bowl and the associated trough.

It is a feature of the lids used in accordance with the invention that they provide one trough for each of the small bowls associated with the trough so that the base section of the trough is arranged in, or on, the opening of the small bowl and provides a well defined clear gap or distance between the bottom portion of the small bowl and the bottom portion of the trough, which gap is partially or completely filled with the sample liquid. Accordingly, there is advantageously provided a well defined layer thickness or layer height of the sample to be analysed because the light beam passes vertically over a well defined path within the sample, without being influenced by the level of filling and the development of menisci. The trough therefore must be configured so that no sample liquid can enter from the small bowl into the trough, ie., the trough must be downwardly and laterally enclosed in liquid impermeable fashion and, accordingly, must be enclosed, for example, by integral sidewalls and a base section, with an upward opening advantageously remaining available. The size and the geometrical form of the troughs are arbitrary and depend particularly upon the size and the geometrical form of the small bowls. According to the invention, it can also be provided to configure the trough of the lid, for example, as a hollow body which is enclosed on all sides and has an opening for filling.

The clear height of the small bowls of the microtitration plates, ie., the distance from the bottom of the small bowl to its upper edge, is reduced by the trough"base section which enters into the small bowl. Since it can be provided in advantageous fashion that all, or many, troughs of the lid have the same dimensions and geometrical forms as the small bowls, all the small bowls, which are partially covered by the base sections of the troughs, are standardised in regard to the path length of the light beam passing vertically through the small bowls, ie., the layer thickness or the layer height, ie., the distance travelled by the vertically passing light beam within the completely filled small bowls or the troughs is given the same value in all covered small bowls, whereby possible differences in the level of filling or the development of menisci are compensated. It can be provided in particularly advantageous fashion that the cross section area of the small bowl, ie., the area perpendicular to the height of filling, is on the level of the small bowl (on which the base section of the trough is situated) greater than the area of the base section of the trough. As a consequence, the base section does not cover the entire clear width of the small bowl in its opening but only part thereof so that sample liquid present in the small bowls can be expelled upwards, whereby nevertheless a light path standardised in regard to its length is ensured.

In the context of the present invention, a microtitration plate is defined as a plate containing a plurality of small bowls, with the small bowls serving to accommodate samples which are subjected to spectrophotometric or fluorometric measurements. The plate and small bowls can be integral with each other but it is also possible to provide that the small bowls are arranged in removable or non removable fashion as separate units or as combined units in a plate and/or frame member. Accordingly, plates and or frames are configured as support means for cuvettes or small bowls or cuvette units or cuvette combinations. The small bowls can be configured as simple depressions, wells, troughs, cuvettes, tubes or the like, and also their cross section shape is arbitrary and therefore can be, for example, circular, polygonal, square, rectangular or oval. The number of small bowls in each microtitration plate is arbitrary, and the small bowls are usually arranged in the form of a matrix, comprising, for example, 96, 384 or 1536 small bowls. In connection with the present invention, a microtitration plate is also understood as an arrangement of small bowls in a row, ie., not in the form of a matrix, and, accordingly, plates having, for example, 8 small bowls or plates having 8 small bowls and being interconnected by web sections are also defined as microtitration plates. The small bowls of the microtitration plate in general have an upward opening so that the samples can be poured in. The small bowls are delimited laterally by sidewalls and downwards by a bottom portion; these elements can be integral with each other.

In connection with the present invention, a substance is understood as a material to be determined on which measurements can be made by spectrophotometric or fluorometric processes, ie., which can be detected and/or quantified, ie., which acts as a chromophore. Such a material to be determined can be formed, for example, by a protein, a peptide, a protein or peptide derivative, a metal complex, a ligand, a dyestuff, a nucleic acid or some other low molecular or macromolecular compound. The microtitration plates to be used in accordance with the invention can be made from any material, e.g., from polyvinylchloride, polystyrene, polypropylene, quartz glass or the like. Of course, it can also be provided to use microtitration plates with coated small bowls.

Thus, the present invention provides a process which facilitates universally applicable, rapid, parallel and therefore low cost studies of interactions of various substances. It is therefore advantageously feasible to determine properties of substances having short half lives. A further advantage results from the fact that concentration effects, which reduce the sensitivity, are minimised and that, furthermore, substances of low solubility can be studied in a better way. Finally, errors due to mixing, which occur in conventional processes, are reduced.

The invention relates also to one of the above described microtitration plates, ie., to a microtitration plate having a plurality of small bowls, with the microtitration plate being associated with a lid having at least one trough associated with a small bowl, with the lid comprising a lid base plate having at least one trough and a preferably substantially flat upper lid plate, and with the upper lid plate adapted to be moved vertically relative to the lid base plate and serving, for covering the trough in the lid base plate. Such a device is advantageous insofar as well defined layer thicknesses can be obtained in both the small bowls of the microtitration plate and the trough of the lid.

The invention also relates to the use of a microtitration plate bearing a plurality of small bowls and a lid, with the lid having at least one trough associated with a small bowl for practising a process for the differential spectroscopical or differential fluorometric measurement of the interaction of substances, with the lid being composed preferably of two plates adapted to be moved vertically relative to each other and with the lower plate containing the troughs.

BRIEF DESCRIPTION OF THE DRAWINGS

The invention will be described in detail with reference to the following embodiments and the respective figures.

The figures show.

DESCRIPTION (OF THE PREFERRED EMBODIMENTS)

In what follows, parts of equal structures or functions are characterised by identical reference numbers.

Figure 1:
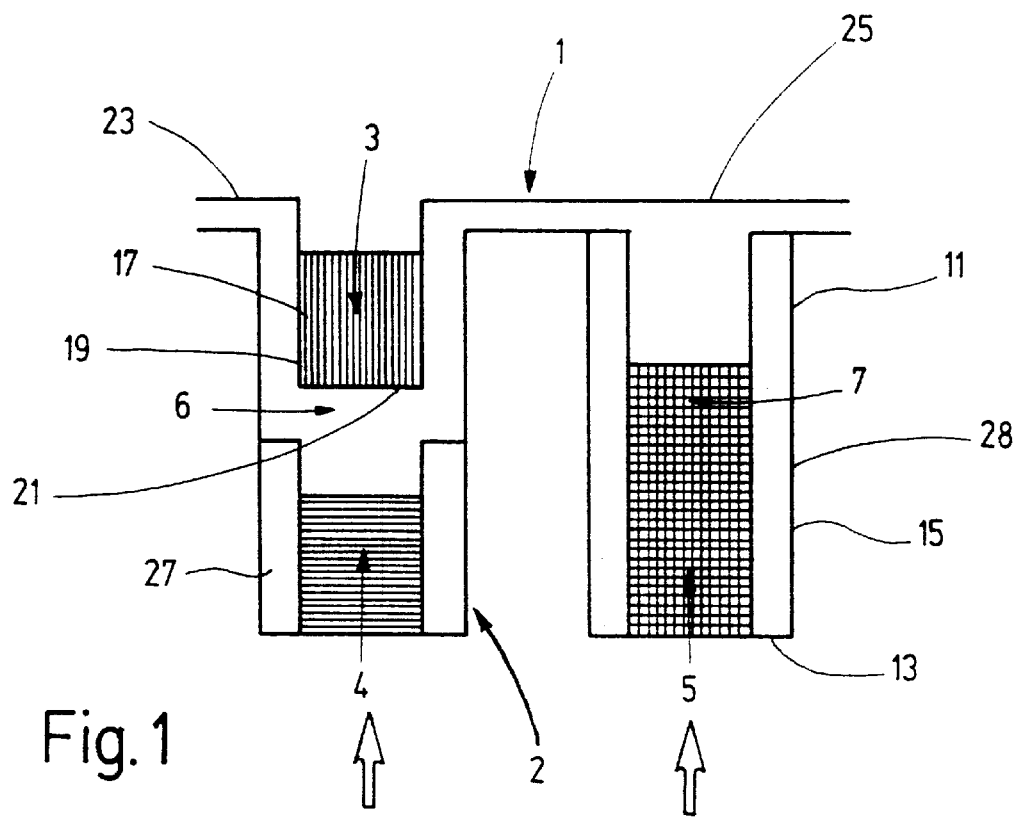
FIG. 1, a vertical section of part of a microtitration plate with a lid, used in accordance with the invention.

FIG. 1 shows a microtitration plate 2 with a lid 1. The microtitration plate 2 bears cylindrical, upwardly open small bowls 11, each composed of a base portion 13 and sidewalls 15. The lid 1 has at least one cylindrical, upwardly open trough 17 associated with a small bowl 11, with the trough 17 being composed of a base section 21 and sidewalls 19. There is also shown the base plate 23 of the lid 1 interconnecting further troughs 17 (not shown) and ensuring accurate positioning or association of the troughs 17 in the small bowls 11. The lid 1 is configured so that at least one small bowl 11 is covered by a flat area 25 without a trough, whereas a further small bowl 11 accommodates the trough 17 of the lid. When the lid 1 has been set onto the microtitration plate 2, in the small bowl 4 which is the left one in FIG. 1, there are formed two vertically superimposed chambers, namely the lower clear space of the small bowl 11 and the clear space of the trough 17. This arrangement of the trough 17 in the clear space of the small bowl 11 can serve for the separate accommodation of solutions and is termed reference region 6. In the microtitration plate's 2 regions, in which the lid 1 is flat and without a trough extending into the clear space of the subjacent small bowl 11, no separate compartments are formed in the clear space of the small bowl 11. This region is termed sample region 7.

In the sample region 7, the clear space of the small bowl 11 has a reinforced sidewall 28 over its entire height and interior periphery. This wall reinforcement reduces the cross section area of the clear space to that of the lower region of the clear space in the small bowl 11 of reference region 6.

There is also shown a sidewall reinforcement 27 extending over the entire internal bowl periphery in the lower region of the clear space of the small bowl 11 within the reference region 6.

This reinforcement serves to create in the lower region of the clear space of the small bowl 11 a cross section area which is as large as the cross section area of the superimposed trough 17.

According to the inventive process, for determining the interaction of two substances A and B, a solution 3 of substance A.is placed into the trough 17 of the lid 1 and a solution 4 of the substance B is put into the clear space of the small bowl 11 under the trough 17, with the volume of the solution 4 being chosen so that the upper edge of the liquid is below the base section of the trough 17. A third solution 5 containing a mixture of solutions .of substances A and B is filled into the sample region 7, ie., into the small bowl 7 which has no associated trough 17, the volume, concentrations, and other parameters are chosen identical with those used for solutions in the reference region 6. Because of the identical geometrical shapes of the troughs and the small bowls in the sample region, there is obtained a layer height corresponding to the added layer heights of the solutions 3 and 4 in the reference region 6. The number and the thickness of the glass or plastic bottom layers penetrated by the light beam, as well as the light path outside the solutions are identical in the sample region and the reference region. After the possibly necessary mixing of the solution in the sample region 7, the interaction of the substances A and B can be analysed with the aid of a spectrophotometer, e.g., an MTP reader, or a fluorometer, by analytic comparison of the spectral or fluorometric properties of the reference region, vertically from the bottom upward or from the top downward (see double arrows). If the fluorometric or spectrophotometric properties vertically determined in the reference region 6 for the separate first and second solutions 3 and 4 are identical with those of the third solution 5 situated in the sample region 7, no interaction has taken place; otherwise the substances A and B interacted.

The microtitration plate 2 with the associated lid 1 for the inventive process as shown in Figure , basically corresponds to the device of FIG. 1. However, in distinction to FIG. 1, in this case the sample region does not differ from the reference region 6, ie., the entire range of the lid 1 has the same structure so that a trough 17 is associated with each of the small bowls 11 in a manner such that the trough extends into the clear space of the small bowl 11. Reference region 6 and sample region 7 are defined only by the type of filling the small bowls 11 and the trough 17. The reference region 6 of the microtitration plate 2 is the region in which the solutions 3, 4 of the sample A and B are measured separately and in vertically superimposed relationship, namely in the lower region of the clear space of a small bowl 11 and in the superimposed clear space of the trough 17. The sample region 7 of the microtitration plate 2 is situated where the third solution 5 is filled in as a mixture of solutions 3 and 4. This may be the lower part of the clear space 11 as well as the trough 17 associated with this small bowl 11. It is also possible to distribute the third solution 5 to trough 17 and small bowl 11. Also in this case, the light irradiation vertical to the base surface of the microtitration plate is indicated by a double arrow.

Figure 2:
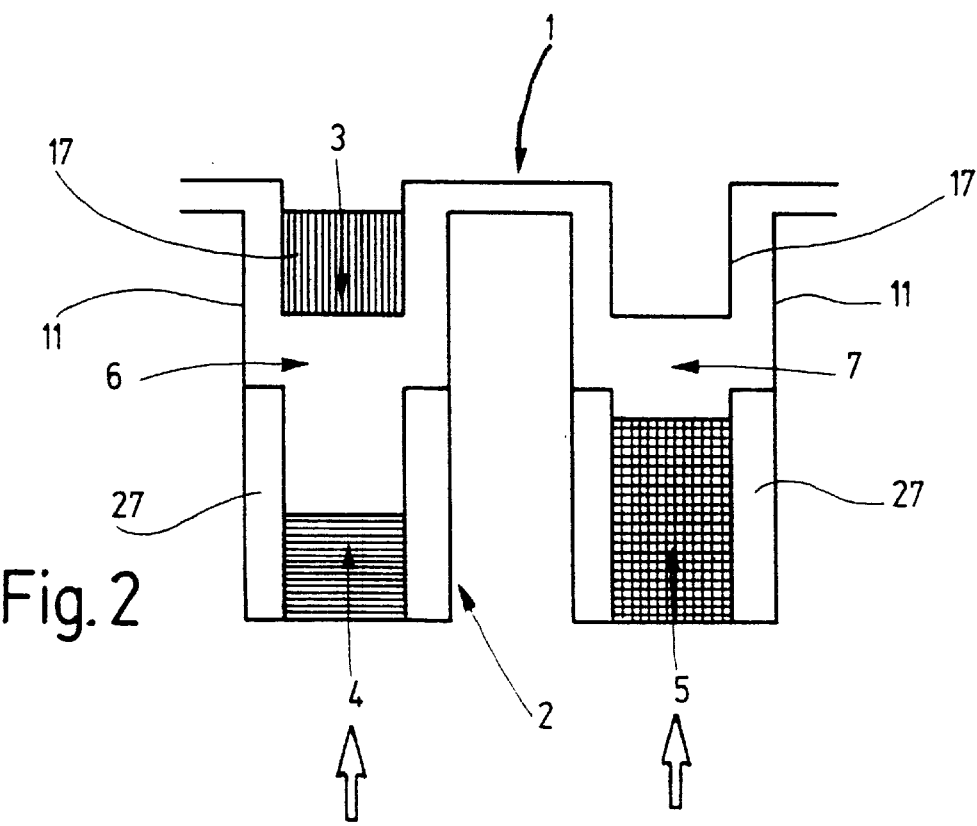
FIG. 2, a vertical section of a part of an other embodiment of a microtitration plate with a lid, used in accordance with the invention.
Figure 3:
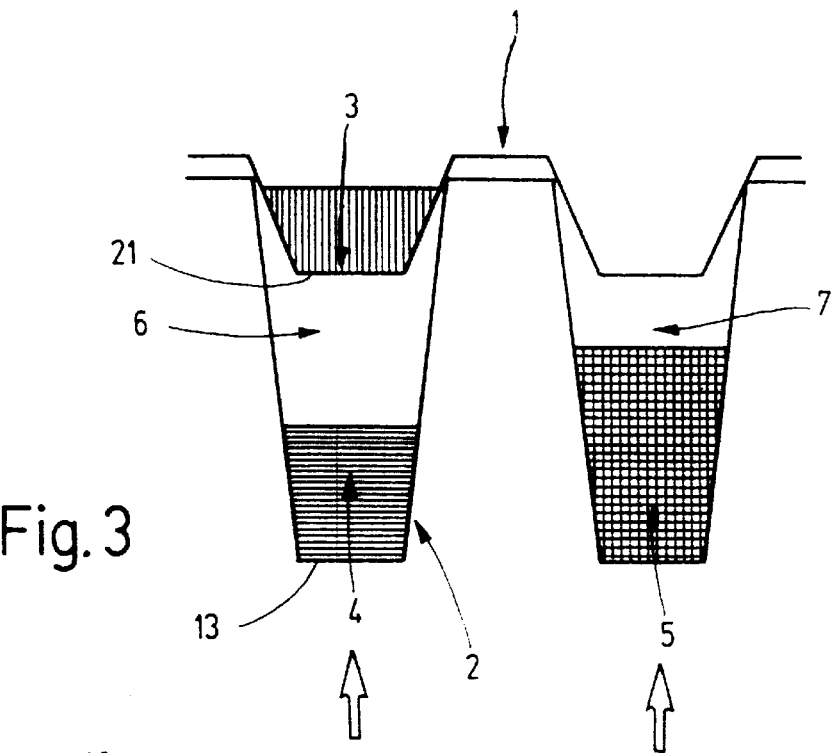
FIG. 3, a vertical section of a part of a further embodiment of a microtitration plate with a lid, used in accordance with the invention.

FIG. 3 shows a further embodiment of a microtitration plate 2 and its lid 1 to be used in accordance with the invention; in distinction to the devices of FIGS. 1 and 2, there are used small bowls 11 and troughs 17 which taper from the top downward, ie., their base sections 21 and 13 have a smaller cross section area than the upper part of their clear space.

Figure 4:
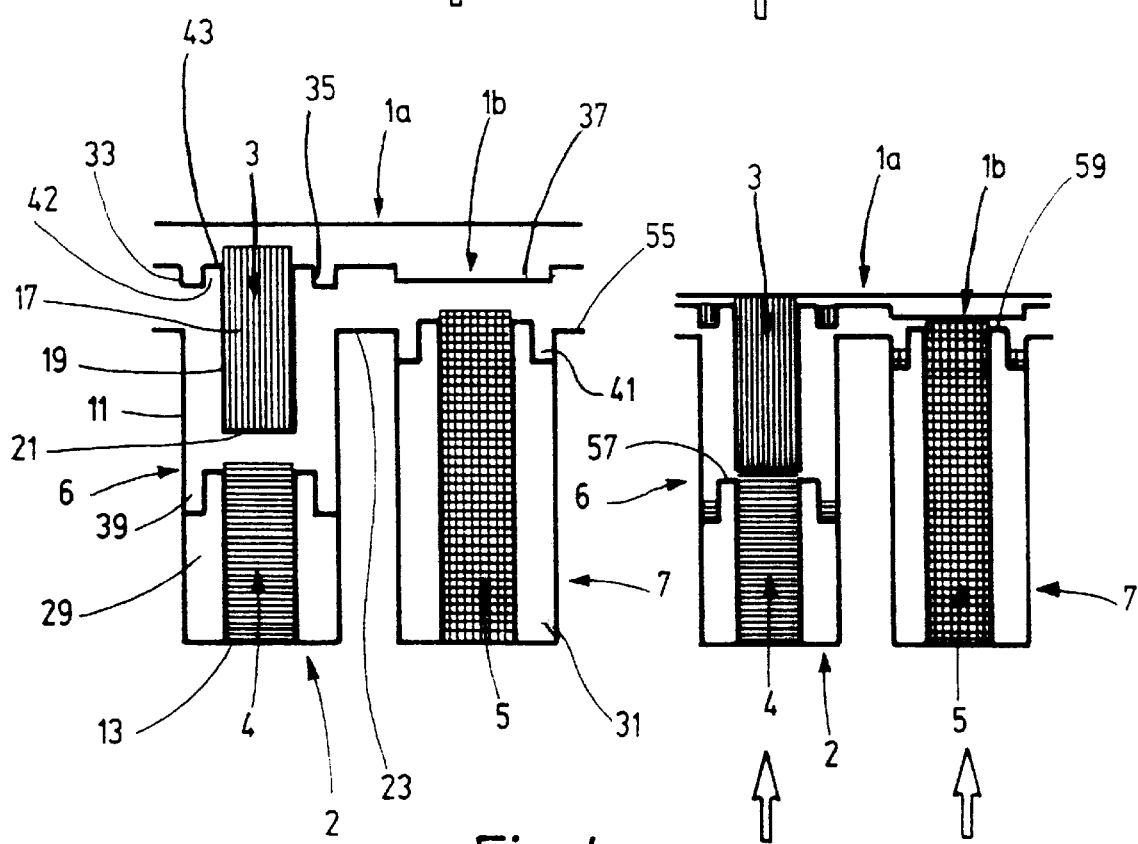
FIG. 4, a vertical section of a part of a further embodiment of the microtitration plate with the lid, used in accordance with the invention, in the opened state and in the closed state.

Also FIG. 4, shows a microtitration plate 2 with a lid 1; the left part of FIG. 4 shows this device in a state in which the lid 1 has not yet been set onto the microtitration plate 2, whereas the right part shows the lid 1 applied to the microtitration plate 2. This microtitration plate has a lid 1 divided into two parts.

The cylindrical small bowl 11 in the reference region 6 of the microtitration plate 2 has in its lower part a sidewall reinforcement 29 which extends over its periphery into the clear space inward and upward to about half the height of the small bowl 11. In the sample region 7 of the microtitration plate 2, there is also provided such a sidewall reinforcement 31 of a cylindrical small bowl 11, with the reinforcement extending upward slightly beyond the upper edge 55 of the microtitration plate 2. In both cases, the wall reinforcement 29 or 31 serves to reduce the clear space. In their boundary regions, the two wall reinforcements 29 and 31 have annular buffer channels or buffer beds 39 and 41.

The lid 1 consists of two parts, a lid base plate 1*b* and a flat lid top part 1*a* arranged on top and adapted to be moved at least in the vertical direction. The plates 1a and 1*b* can be connected by screw connections or clamping connections, hinges or the like. Plate 1*a* may also be just set onto the lid base plate 1*b*. The lid base plate 1*b* defines the cylindrical trough 17, ie., its sidewalls 19 and the base section 21. Trough 17 is surrounded by a buffer bed 35 in ring form, separated by an annular wall 42 from the trough. The cross section area of the base section 21 corresponds to the cross section area of the clear space of the base portion 13 of the small bowl 11. In an other region of the lid base plate 1*b*, there is provided a flat surface 37 in place of the trough 17.

The lid 1 is applied to the microtitration plate 2 in a manner such that the trough 17 extends into the clear space of a small bowl 11 situated within the reference region 6, ie., into a small bowl 11 the wall reinforcement 29 of which extends only to about half of the height. The flat region 17 of the lid base plate 1*b* in the sample region 7 closes upwardly the clear space of the small bowl 11 in the closed or in the applied state, with the wall reinforcement 31 of the small bowl extending slightly above the upper edge 55 of the base plate 23 of the microtitration plate 2.

When a solution 3 is filled into the trough 17 in the reference region 6, a solution 4 is filled into the lower part of the clear space of the small bowl 11 in the reference region 6, and the third solution 5 is filled into the sample region 7 of an other small bowl 11 and when the lid is applied, the bottom section 21 of the trough 17 is seated directly on the upper edge of the wall reinforcement 29 in the lower part of the small bowl 11 or is flush with the same and, provided that sufficient sample liquid 4 has been filled in, prevents a detrimental development of menisci and different levels of filling. Thus, a well defined layer height is provided. An arrangement with a similar structure in other small bowls 11 (not shown) facilitates standardisation of the layer heights and, hence, reduces measurement errors. Sample liquid 4, which was possibly expelled upon filling in the sample or during application of the lid, is diverted into the buffer bed 39 moulded as a ring into the upper part of the wall reinforcement 29. Similarly, in the closed state, the flat surface 37 of the lid base plate 1*b* rests on the upper edge 59 of the wall reinforcement 31 of the small bowl 11 in the sample region 7 in order to prevent the development of menisci at appropriate filling levels and different levels of filling and also to ensure a well defined layer height. Third solution 5, which might have been expelled, is diverted into the annular buffer bed 41 in the upper region of the reinforcement 31. In the closed state, the lid top part 1*a* rests on the lid base plate 1*b* and is attached, if necessary, with the lid top part 1*a* being flush with the upper edge 43 of the wall 42 and preventing, in the case of complete filling, the development of detrimental menisci and different levels of filling. Sample liquid 3, which might have been expelled, is diverted into the buffer bed 35 which in the lid base plate 1b is situated in the form of a ring around the trough 17. It is ensured in this way that the light can pass through both the separated solutions 3 and 4 and the third solution 5 without being affected by sources of errors such as different levels of filling or the development of menisci.

Thus, the device according to FIG. 4 makes it possible to practice the inventive process with standardised layer heights in both the reference region 6 and the sample region 7 and is therefore suitable particularly for parallel, efficient, and accurate differential spectroscopical or differential fluorometric measurements. Standardisation of the layer heights also in the troughs 17 of the lid is obtained by the lid 1 divided into two parts and proves to be particularly advantageous. Processes according to the invention, making use of this device, ie., of a device with means, e.g., a flat plate 1a, for standardising the layer height in a trough 17 of the lid 1, are therefore advantageous and especially suitable for automated measurements.

What is claimed is:

1. A process for differential spectroscopical or differential fluorometric determination of the interaction of at least two different substances, comprising:

providing a micro-titration plate having a plurality of small bowls and a respective lid over at least a first one of the bowls, wherein the lid includes at least a first trough associated with the first bowl;

filling a first solution of a first substance into the first bowl;

filling a second solution of a second substance into the first trough in the lid, wherein the first trough is associated with the first bowl;

filling a third solution containing a mixture of the first and the second substances into a second one of the small bowls or a second trough in the lid over the plate;

subsequently performing the differential spectroscopical or differential fluorometric measurement by vertically irradiating electromatic waves through the first and second small bowls and the first and second troughs in the lid associated with the small bowls.

2. The process of claim 1, further comprising preparing the third solution to be filled by mixing a solution of the first substance with a solution of the second substance and wherein at least one of a volume and a substance concentration of the first and second solutions in the third solution is equal to the respective at least one of a volume and a substance concentration of the first and the second solutions in the first bowl and the first trough, respectively.

3. The process of claim 1, wherein filling the third solution comprises filling tie one of the second small bowl and the trough that receives the third solution to a layer height equal to the sum of layer heights of the first and the second solutions in the first small bowl and the first trough, respectively.

4. The process of claim 1, wherein the first, second and third solutions have heights in the respective ones of the first and second bowls and troughs which heights are standardized.

5. The process of claim 1, comprising placing the lid over the plate such that the first trough is over the first bowl and there is no trough of the lid over the second bowl.

6. A device for differential spectroscopical or differential fluorometric determination of the interaction of at least two different substances, comprising a micro-titration plate having at least a first and second small bowl, a lid over the plate, the lid having a trough and the lid being disposed so that the trough is above the first bowl;

the lid having a base plate comprising the at least one trough and the lid including a top plate adapted to move vertically relative to the lid base plate.

* * * * *